United States Patent [19]
Wagner et al.

[11] Patent Number: 5,938,604
[45] Date of Patent: Aug. 17, 1999

[54] RADIOACTIVE NEEDLE FOR BIOPSY LOCALIZATION AND A METHOD FOR MAKING THE RADIOACTIVE NEEDLE

[75] Inventors: Robert Hans Wagner, Burr Ridge; Stephen Maxwell Karesh, Chicago, both of Ill.

[73] Assignee: Capintec, Inc., Ramsey, N.J.

[21] Appl. No.: 08/864,120

[22] Filed: May 28, 1997

[51] Int. Cl.⁶ .................................................. A61B 6/00
[52] U.S. Cl. .............................................. 600/436; 427/5
[58] Field of Search ................................. 600/436, 1, 3, 600/7, 431; 427/5

[56] References Cited

U.S. PATENT DOCUMENTS

| | | | |
|---|---|---|---|
| 3,674,006 | 7/1972 | Holmer | 600/7 |
| 4,508,119 | 4/1985 | Tukamoto | 606/189 |
| 4,781,198 | 11/1988 | Kanabrocki | 600/431 |
| 5,342,283 | 8/1994 | Good | 600/8 |
| 5,647,374 | 7/1997 | Cutrer | 600/431 |

OTHER PUBLICATIONS

Article, "Nuclear Medicine: Radiolabeled Needles Locate Scintigraphic Abnormalities", Advance Magazine, May 1998, p. 14.

*Primary Examiner*—Brian L. Casler
*Attorney, Agent, or Firm*—Evenson, McKeown, Edwards & Lenahan, PLLC

[57] ABSTRACT

A needle tipped with a plating of radioactive metal and covered with additional layers of plating to prevent subsequent rubbing off of radioactive material, decreases local or systemic reactions to the plating materials, and prevents decomposition of the underlying plating materials. The radioactive tipped needle can be used in conjunction with nuclear medicine imaging techniques to identify and localize abnormalities that may not be seen using other radiographic techniques. A method for producing the needle is also described.

9 Claims, 4 Drawing Sheets

RADIOACTIVE NEEDLE FOR BIOPSY LOCALIZATION AND A METHOD FOR MAKING THE RADIOACTIVE NEEDLE

FIELD OF THE INVENTION

This invention relates to needle localization for biopsy, specifically to enable localization of an abnormality seen using nuclear medicine imaging techniques.

BACKGROUND OF THE INVENTION

The medical speciality of diagnostic radiology has long had the ability to observe abnormalities using x-rays or x-ray fluoroscopy. These abnormalities can often be biopsied or localized in preparation of surgery because both the abnormality and the metallic needle can be seen under x-rays.

The nature of nuclear medicine imaging techniques allows the abnormality to be seen, but non-radioactive materials or objects such as a conventional biopsy needles cannot be seen. To allow pre-surgical localization or biopsy using nuclear medicine techniques, a radioactive needle must be used.

In U.S. Pat. No. 4,781,198 issued to Kanabrocki, a biopsy needle for this purpose is described. This needle is coated with a radioactive metal and then subsequently coated with another layer of stable metal. The problem with this approach is that for use in the human body, the outer layer must be as chemically non-reactive as possible. Some of the metals that can be plated are highly toxic or irritating to the skin. To be useful in humans, the outer layer must therefore be composed of a biologically and chemically inert material such as gold. If the needle is to be stored for any length of time prior to use, the outer layer must also prevent any chemical oxidation from occurring and must be able to tolerate sterilization procedures.

A standard stainless steel needle cannot be plated with gold without prior surface preparation, as gold is not readily adherent to stainless steel. The needle as described by Kanabrocki is functional, but lacks the means by which an outer layer of gold can be plated onto it.

SUMMARY OF THE INVENTION

The objects and advantages of the present invention include:

(a) to provide a mechanism where pre-surgical localization or biopsy of abnormalities can be performed using nuclear medicine techniques;

(b) to provide an object that is biologically inert so as to prevent the possibility of local allergic or systemic reactions resulting from the introduction of a foreign body;

(c) to prevent the oxidative decomposition of the underlying materials by covering the needle with a chemically non-reactive material such as gold; and (d) to provide a means by which the plated radioactive material will not dissociate from the needle during placement or removal.

The invention provides a metallic needle including a shaft and a tip, including a layer of radioactive material covering the tip of the needle, the radioactive material being visible under a nuclear medicine imaging device; and having an outer layer of metal as a coating on the needle and the layer of radioactive material. The needle may also, optionally, include at least one intermediate layer of metal coated on the layer of radioactive material. The surface of the outer layer of metal on the needle is biologically non-reactive and resists chemical decomposition of layers underlying said outer layer of metal. The needle may be a hollow needle or a solid needle.

The invention also provides a method for producing a metallic needle having a radioactive tip for use with nuclear medicine imaging techniques including immersing a metallic needle in a solution of radioactive material; applying electrical current and voltage, thereby causing radioactive material to be deposited on the needle or, alternatively, causing chemical deposition of the radioactive material on the needle; and immersing the needle having the radioactive material deposited thereon in a solution of a metal that is biologically non-reactive in its metal form, thereby forming an outer metallic layer that is biologically non-reactive on the needle. The method may optionally include immersing the needle having the radioactive material deposited thereon in a metallic solution and causing deposition of a metallic intermediate layer thereon by electrical deposition or chemical deposition. The outer metallic layer may also be applied by electrical deposition or chemical deposition.

BRIEF DESCRIPTION OF THE DRAWINGS

In the following figures, closely related elements have the same number, but different alphabetic suffixes.

DETAILED DESCRIPTION OF THE PREFERRED EMBODIMENTS

Figure 1:
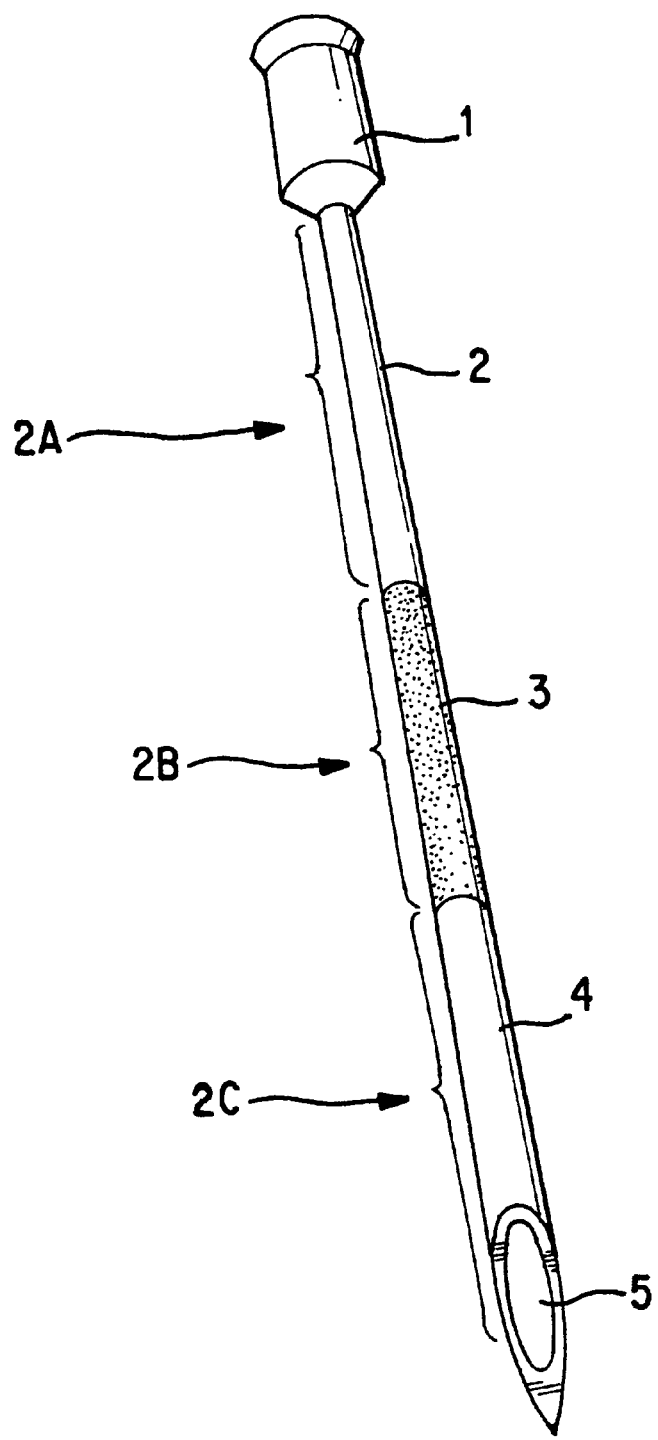
FIG. 1 shows the needle after the plating process is complete.

A typical example of the radioactive needle 1 is illustrated in FIG. 1. The needle has a tubular shaft of metal 2 terminating in a needle point with an opening 5 that runs the length of the tubular shaft. The tubular shaft 2 is most commonly comprised of stainless steel. This is connected to a needle hub 1 that can be made of either metal or plastic. The needle hub is securely fastened to the tubular shaft 2. The needle hub 1 can be attached to a syringe by the user. The tubular shaft is plated with layers of various metals. For the purpose of illustration, the plated area of the needle portion having intermediate plating and outer plating 3 and the plated area of the needle portion having radioactive plating, intermediate plating and outer plating 4 are colored differently. Plated area 4 is part of the tubular shaft 2 plated with a layer of radioactive metal which is covered by an intermediate layer of plating material such as nickel and an outer layer of plating material such as gold. Plated area 3 is part of the tubular shaft 2 plated only with the intermediate layer such as nickel and outer layer such as gold. Since areas 3 and 4 are both plated with the same outer layer of material, they will be visually indistinguishable.

Figure 2A:
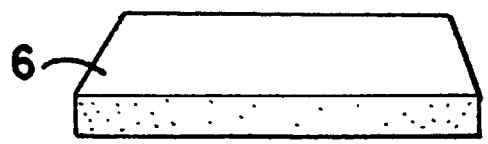
FIGS. 2A through 2C show cross sections of the needle at the atomic level at the sites specified as A, B, and C on FIG. 1.
Figure 2B:
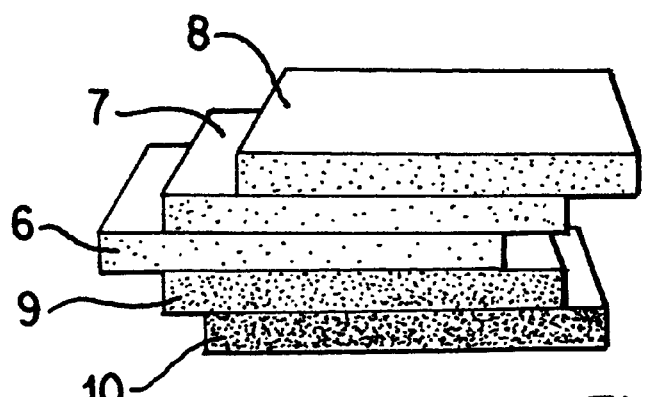
Figure 2C:
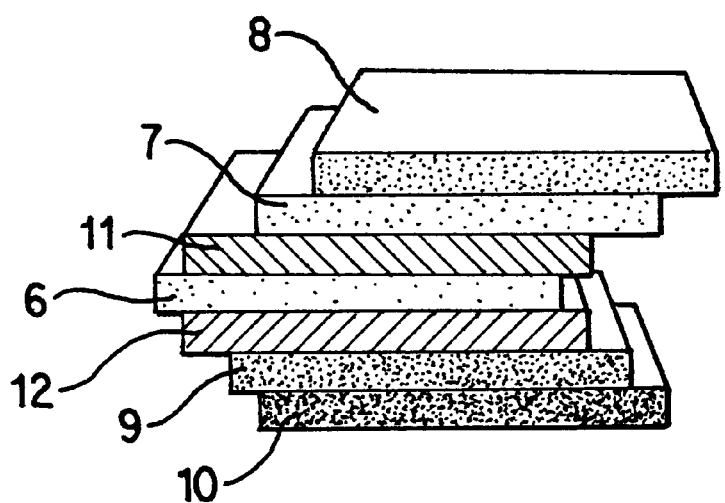

FIGS. 2A–C reflect cross sections at the atomic level of the tubular shaft illustrated in FIG. 1 at points A, B, and C in FIG. 1. The cross section of the tubular shaft 6 is in reality many times thicker than the layers of plating 7–12. FIG. 2B reflects a cross section of the tubular shaft at point B on FIG. 1. Layers 7 and 9 are the intermediate layers of plating on the exterior and interior of the tubular shaft, respectively. Layers 8 and 10 are the outer layers of plating on the exterior and interior of the tubular shaft, respectively. FIG. 2C reflects a cross section of the tubular shaft 2 at point C in FIG. 1. Layers 11 and 12 are the radioactive metal that is plated onto the exterior and interior of the tubular shaft, respectively, before being covered with layers 7–10.

Figure 3A:
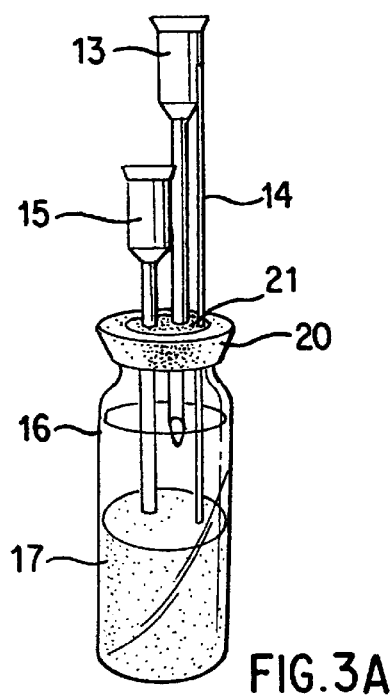
FIGS. 3A through 3C, show the setup of the apparatus necessary to perform the plating.

FIG. 3A illustrates a first step in the production of the radioactive needle. This step is the plating of radioactive metal onto the tubular shaft 2 and can be performed in a 10 ml glass vial 16 with metal overseal 20 and coated rubber septum 21. The glass vial is filled with 3 ml of radioactive metal solution. The chemical composition and radioconcentration of the plating solution varies depending on the radioactive metal desired to be plated and the resulting amount of radioactivity desired on the needle. The chemistry of electroplating is well documented in the literature. There is no difference in the chemistry when plating a radioactive or a non-radioactive metal. The needle 15 that is to be plated is placed through the rubber coated septum 21 so that the tip of the needle is submerged into the radioactive metal plating solution 17. A hollow ventilation needle 13 which can be of the same design as the needle to be plated 15 is placed through the rubber coated septum 21, but should not come into contact with radioactive metal solution 17. A metallic conductive rod 14 is also placed through the rubber coated septum 21 and is submerged into the radioactive metal solution. The hollow needle 13, the metallic conductive rod 14 and the needle 15 to be plated are not allowed to come into contact with each other or with the metal overseal for the vial 20. The metallic conductive rod 14 and the needle 15 to be plated are connected to a direct current power source. The needle 15 to be plated is connected to the cathode (negatively charged terminal) of the power source while the metallic conductive rod 14 is connected to the anode (positively charged terminal) of the power source. The duration of electrolysis and the operating voltage are dependent upon the composition of the solution, but are usually in the range of several minutes of duration with a voltage of about 3–12 volts DC.

Figure 3B:
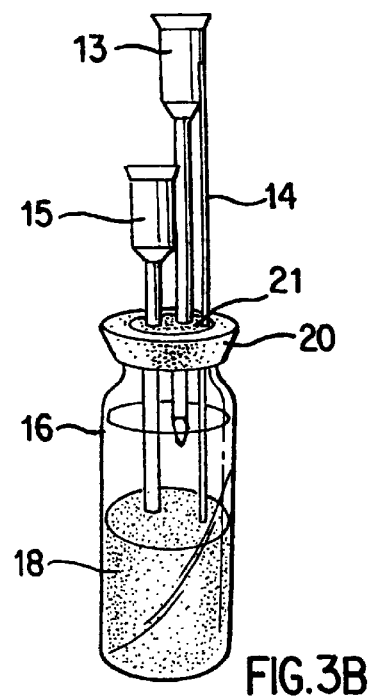

When plating of the radioactive metal is completed, the needle 15 is removed and washed with water. The bore of the needle is rinsed by connecting with a syringe of at least 10 ml volume and flushing the water through the needle. The needle is then dried and replaced into a different vial as in FIG. 3B. In FIG. 3B, the plating solution 18 is the intermediate layer plating solution. The volume of solution 18 is about 5–6 ml. and the needle 15 to be plated is inserted through the rubber coated septum 21. The tip of the needle 15 to be plated is placed near the bottom of the vial 16. In this manner, the plating solution covers a longer length of the needle than in FIG. 3A. The cathode and anode are again attached to the needle 15 and the conductive rod 14, respectively, and voltage is applied. The duration of plating and the voltage are dependent upon the solution used. When plating is complete, the needle 15 is again removed, rinsed with water and dried as described above.

Figure 3C:
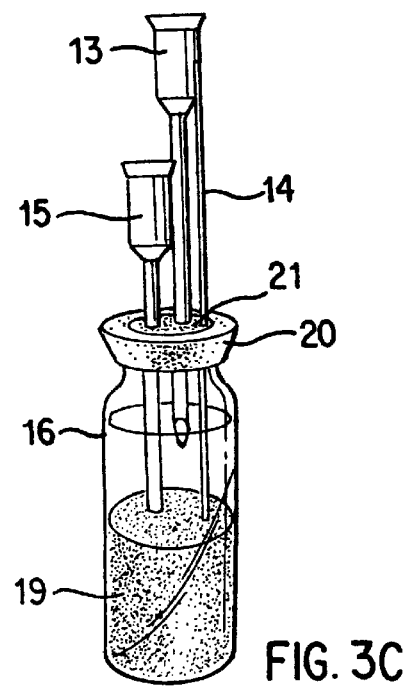

The needle 15 to be plated is placed into the final assembly as in FIG. 3C. In this case, the solution contains the outer plating material 19 in a volume of about 7 to 8 ml. The tip of the needle 15 is again placed near the bottom of the vial. The plating solution 19 thus covers a longer length of the needle than in the prior two steps. The cathode and anode are attached as described above and voltage is applied. The duration of plating and the voltage are again dependent on the solution used. When plating is complete, the needle 15 is removed and dried. The needle 15 is then assayed for the amount of radioactivity and sterilized prior to usage.

Although closed systems are used in the process described above for production of the radioactive plated needle, it can equally be performed in an open system (without vial top and rubber septum) without the need for a hollow ventilation needle 13.

Figure 4A:
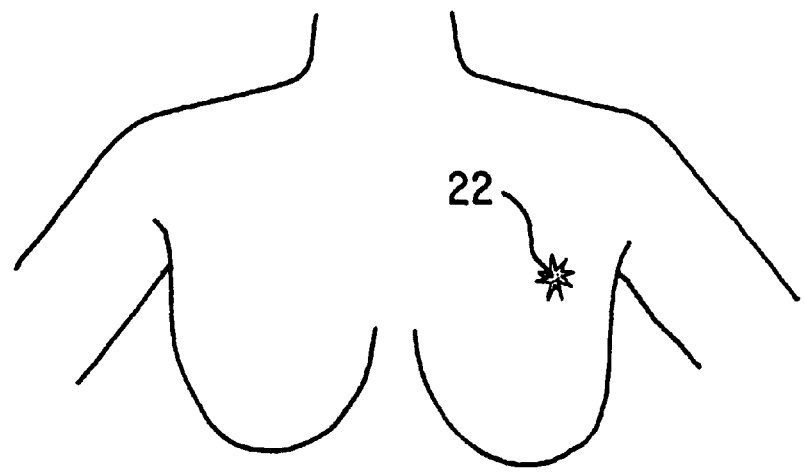
FIG. 4A is a sketch of a person with an abnormality in the left breast.
Figure 4B:
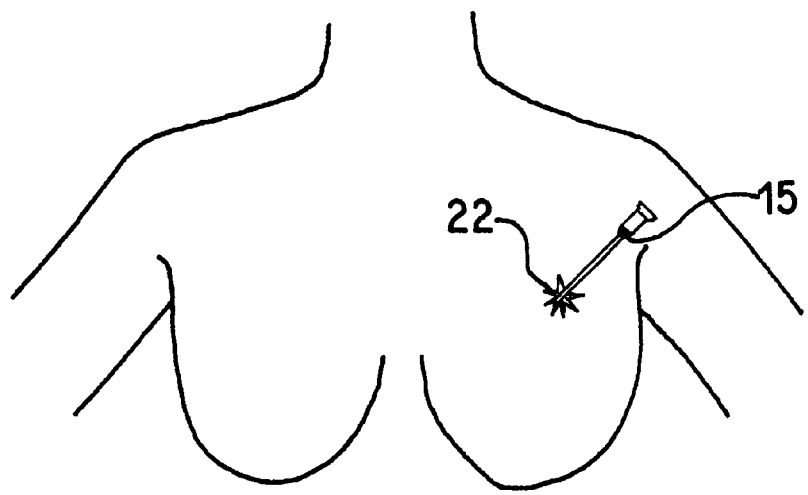
FIG. 4B shows the needle being used to localize the abnormality.

FIG. 4A illustrates an individual with an abnormality 22 in a breast. This abnormality 22 must be able to be visualized using conventional nuclear medicine scanning procedures. Using a nuclear medicine camera and sterile technique, the physician inserts the radioactive needle 15 into the breast in close proximity to the abnormality 22, as shown in FIG. 4B. The needle may be removed or repositioned as necessary to bring the tip of the needle as close as possible to the abnormality 22. Once positioning is assured, an anchoring wire such as is used in conventional mammography, or injection of a marking solution can be used to assist the surgeon in identifying the abnormality 22.

EXAMPLES

The following are examples of plating solutions, useful in the apparatus shown in FIGS. 3A—3C.

Plating Solution 17—FIG. 3A
10 mCi of Tc99m in 3 ml of distilled water
Voltage: 12 Volt DC
Amperage: 5–7 mA
Time: 5 minutes
Plating Solution 18—FIG. 3B
10 ml of 0.1M solution of $NiCl_2$
2 ml of $H_2SO_4$ (31.5 g/l)
Voltage: 3 Volts DC
Amperage: 100 mA
Time: 2 minutes
Plating Solution 19—FIG. 3C
10 ml of 0.005M solution of $AuCi_3$
2 ml of $H_2SO_4$ (31.5 g/l)
Voltage: 4 Volts DC
Amperage: 100 mA
Time: 1 minute
Conclusions From the above description, it is seen that the radioactive needle described herein can be used in a variety of medical situations where an abnormality can be seen on nuclear medicine imaging but may not be seen on standard radiographic imaging. The non-limiting example in FIG. 4 pertains to an abnormality in the breast that is seen on nuclear medicine imaging but is either not seen or is only seen to be of questionable significance on standard mammography. The technique can also be used to localize other areas of infection or tumor involvement that are seen using nuclear medicine techniques but are not seen or are seen to be only of questionable significance using radiographic techniques.

The apparatus described above has the following advantages:

1. it provides a mechanism whereby a physician skilled in nuclear medicine can localize abnormalities that cannot be detected or properly evaluated using other techniques;

2. the outer plating of non-reactive metal such as gold will decrease the incidence of local reaction from the materials that are plated onto the needle;

3. the outer plating of non-reactive metal will seal the radioactivity and intermediate layers beneath it and prevent the possibility of chemical reactions during the sterilization process or storage;

4. the outer layer of non-reactive material and the intermediate layer of material will prevent removal of any of the radioactive material during use of the needle.

Although the above description contains many specificities, these should not be construed as limiting the scope or utility of the invention, but merely provide illustrations of some of the possible uses for a radioactive needle. For example, the tip of a standard biopsy needle can be labeled and a biopsy performed using nuclear medicine imaging as guidance. Another possibility is the labeling of the tip of a standard needle used for needle localization of a breast abnormality. The anchoring wire for the needle can be placed once the positioning of the needle tip is assured.

The above description of producing a radioactive needle should not be construed as the only method of producing the radioactive needle. The above described process utilizes the method of electroplating. Other processes such as electroless plating can also be used to achieve the same effect.

The scope of the invention should be determined by the appended claims and their equivalents, rather than by the examples given.

What is claimed is:

1. A method for producing a metallic needle having a radioactive tip for use with nuclear medicine imaging techniques comprising:

immersing a metallic needle in a solution of radioactive material;

applying electrical current and voltage, thereby causing radioactive material to be deposited on said needle;

immersing said needle having said radioactive material deposited thereon in a metallic solution and causing deposition of a metallic intermediate layer thereon by a method selected from the group consisting of electrical deposition and chemical deposition; and immersing said needle having said radioactive material and said metallic intermediate layer deposited thereon in a solution of a metal that is biologically non-reactive in its metal form, thereby forming an outer metallic layer that is biologically non-reactive on said needle.

2. A method according to claim 1, wherein said outer metallic layer is applied by a method selected from the group consisting of electrical deposition and chemical deposition.

3. A method for producing a metallic needle having a radioactive tip for use with nuclear medicine imaging techniques comprising:

immersing a metallic needle in a solution of radioactive material;

causing chemical deposition of said radioactive material on said needle;

immersing said needle having said radioactive material deposited thereon in a metallic solution and causing deposition of a metallic intermediate layer thereon my a method selected from the group consisting of electrical deposition and chemical deposition; and immersing said needle having said radioactive material and said metallic intermediate layer deposited thereon in a solution of a metal that is biologically non-reactive in its metal form, thereby forming an outer metallic layer that is biologically non-reactive on said needle.

4. A method according to claim 3, wherein said outer metallic layer is applied by a method selected from the group consisting of electrical deposition and chemical deposition.

5. A metallic needle including a shaft and a tip, said needle comprising:

a layer of radioactive material covering said tip of said needle, said radioactive material being visible under a nuclear medicine imagine device;

at least one intermediate layer of metal coated on said layer of radioactive material; and an outer layer of metal as a coating on said needle and said layer of radioactive material and said intermediate layer of metal.

6. A needle according to claim 5, wherein a surface of said outer layer of metal is biologically nonreactive.

7. A needle according to claim 5, wherein a surface of said outer layer of metal resists chemical decomposition of layers underlying said outer layer of metal.

8. A needle according to claim 5, comprising a hollow needle.

9. A needle according to claim 5, comprising a solid needle.

\* \* \* \* \*